(12) United States Patent
L'Alloret

(10) Patent No.: US 6,905,674 B2
(45) Date of Patent: *Jun. 14, 2005

(54) AQUEOUS PHOTOPROTECTIVE COMPOSITIONS COMPRISING ACRYLAMIDO-2-METHYLPROPANESULFONIC ACID POLYMERS AND 4,4-DIARYLBUTADIENE UV-A SUNSCREENS

(75) Inventor: Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/823,670

(22) Filed: Apr. 14, 2004

(65) Prior Publication Data

US 2004/0228815 A1 Nov. 18, 2004

Related U.S. Application Data

(60) Provisional application No. 60/468,089, filed on May 6, 2003.

(30) Foreign Application Priority Data

Apr. 14, 2003 (FR) .............................................. 03 04647

(51) Int. Cl.$^7$ .............................. A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS

| 6,436,373 B1 | 8/2002 | Habeck et al. |
| 2003/0031643 A1 | 2/2003 | L'Alloret et al. |

FOREIGN PATENT DOCUMENTS

| DE | 198 920 116 A1 | 11/1999 |
| DE | 100 07 017 A1 | 8/2001 |
| DE | 101 24 914 A1 | 11/2002 |

OTHER PUBLICATIONS

French Search Report Issued in French Priority Counterpart FR 03/04647 on Dec. 9, 2003, 2 pages.

*Primary Examiner*—Shelley A. Dodson
(74) *Attorney, Agent, or Firm*—Burns, Doane, Swecker & Mathis, L.L.P.

(57) ABSTRACT

Photoprotective compositions, e.g., oil-in-water or water-in-oil emulsions, well suited for the photoprotection of the skin, lips and/or hair against the damaging effects of UV-radiation, comprise at least one aqueous phase, at least one oily phase, at least one partially or completely neutralized, crosslinked or non-crosslinked water-soluble or water-dispersible acrylamido-2-methylpropanesulfonic acid (AMPS) polymer and at least one UV radiation-screening system, said at least one screening system comprising at least one 4,4-diarylbutadiene UV-A-screening agent

49 Claims, No Drawings

US 6,905,674 B2

AQUEOUS PHOTOPROTECTIVE COMPOSITIONS COMPRISING ACRYLAMIDO-2-METHYLPROPANESULFONIC ACID POLYMERS AND 4,4-DIARYLBUTADIENE UV-A SUNSCREENS

CROSS-REFERENCE TO PRIORITY/PROVISIONAL APPLICATIONS

This application claims priority under 35 U.S.C. § 119 of FR 03/04647, filed Apr. 14, 2003, and of provisional application Ser. No. 60/468,089, filed May 6, 2003, both hereby expressly incorporated by reference and both assigned to the assignee hereof. This application is also a continuation of said '089 provisional.

BACKGROUND OF THE INVENTION

1. Technical Field of the Invention

The present invention relates to photoprotective compositions comprising at least one aqueous phase, at least one oily phase, at least one water-soluble or water-dispersible, partially or completely neutralized, crosslinked or non-crosslinked acrylamido-2-methylpropanesulfonic acid polymer and at least one UV radiation-screening system, which screening system comprises at least one UV-A-screening agent of the 4,4-diarylbutadiene type.

2. Description of Background and/or Related and/or Prior Art

It is well known that light radiation having wavelengths of between 280 nm and 400 nm allows tanning of the human epidermis, and that rays having wavelengths of between 280 nm and 320 nm, known by the name UV-B, cause erythemas and skin burns which can hamper the development of the natural tan; this UV-B radiation must therefore be screened out.

It is also known that UV-A rays having wavelengths of between 320 nm and 400 nm, which cause tanning of the skin, are capable of inducing its impairment, in particular in the case of a sensitive skin or a skin continually exposed to solar radiation. UV-A rays cause in particular a loss of elasticity of the skin and the appearance of wrinkles which lead to premature aging. They promote the onset of the erythematous reaction or amplify this reaction in some subjects and may even be responsible for phototoxic or photoallergic reactions. It is therefore desirable to also screen out UV-A radiation.

UV-A and UV-B rays must therefore be screened out and protective cosmetic compositions for the human epidermis containing UV-A and UV-B screening agents currently exist.

These anti-sun compositions are often provided in the form of an emulsion of the oil-in-water type (that is to say a cosmetically and/or dermatologically acceptable carrier consisting of an aqueous dispersive continuous phase and a fatty dispersed discontinuous phase) or of the water-in-oil type (aqueous phase dispersed in a continuous fatty phase), which contains, in various concentrations, one or more conventional fat-soluble organic screening agents and/or conventional water soluble organic screening agents capable of selectively absorbing harmful UV radiation, these screening agents (and their quantities) being selected according to the desired sun protection factor, the sun protection factor (SPF) being mathematically expressed by the ratio of the dose of UV radiation necessary to reach the erythematogenic threshold with the UV-screening agent to the dose of UV radiation necessary to reach the erythematogenic threshold without UV-screening agent. In such emulsions, the hydrophilic screening agents are present in the aqueous phase and the lipophilic screening agents are present in the fatty phase.

Acrylamido-2-methylpropanesulfonic acid (AMPS) polymers are particularly suited for their cosmetic properties and their flexibility in terms of formulation, compared with the polymeric derivatives of the carboxylic acid (Carbopols supplied by Noveon). They may indeed be formulated at pH values of between 4 and 6 without their gelling properties being reduced. Among these derivatives, two large families may be mentioned:

(a) the hydrophilic or water-dispersible polymers such as neutralized and crosslinked polyacrylamido-2-methylpropanesulfonic acid supplied by Clariant under the name Hostacerin AMPS, or the copolymers of AMPS and other hydrophilic monomer(s) such as Sepigel 305 supplied by SEPPIC and Aristoflex AVC supplied by Clariant;

(b) the amphiphilic polymers comprising AMPS and alkyl recurring units such as those described in EP-1,069,142.

These acrylamido-2-methylpropanesulfonic acid polymers are particularly suitable in the manufacture of emulsions. They make it possible to obtain stable formulations within a broad range of texture and consistency ranging from milks to thickened creams.

Among the organic UV-A-screening agents available, a family of compounds which are particularly effective in the UV-A region is 1,4-benzene[di(3-methylidene-10-camphorsulfonic)]acid and its various salts, described in particular in FR-A-2,528,420 and FR-A-2,639,347; they are indeed capable of absorbing ultraviolet rays having wavelengths of between 280 nm and 400 nm, with absorption maxima of between 320 nm and 400 nm, in particular in the region of 345 nm.

However, the introduction of this type of UV-A-screening agent into photoprotective emulsions stabilized and/or thickened with an acrylamido-2-methylpropanesulfonic acid polymer can lead to a significant reduction in their viscosity or to their destabilization.

It thus appears necessary to have emulsions based on acrylamido-2-methylpropanesulfonic acid polymers which are stable and which may contain organic screening agents which are active in UV-A with comparable efficacy to that of 1,4-benzene[di(3-methylidene-10-camphorsulfonic)] acid and its different salts without the disadvantages listed above.

The expression "stable" is understood to mean that the macroscopic and microscopic appearance of the composition is not modified after 1 month at room temperature.

SUMMARY OF THE INVENTION

It has now surprisingly and unexpectedly been determined that emulsions comprising at least one partially or completely neutralized, crosslinked or non-crosslinked acrylamido-2-methylpropanesulfonic acid polymer and at least one UV-A-screening agent of the 4,4-diarylbutadiene type ameliorate or avoid those disadvantages and drawbacks indicated above.

In the remainder of the present description, the expression "UV radiation-screening system" is understood to mean a UV radiation-screening agent comprising either a single organic or inorganic compound screening out UV radiation or a mixture of several organic or inorganic compounds screening out UV radiation, for example a mixture comprising a UV-A-screening agent and a UV-B-screening agent.

This discovery forms the basis of the present invention.

Thus, the present invention features photoprotective compositions comprising at least one aqueous phase, at least one oily phase, at least one partially or completely neutralized, crosslinked or non-crosslinked water-soluble or water-dispersible acrylamido-2-methylpropanesulfonic acid polymer and at least one UV radiation-screening system, which screening system comprises at least one UV-A-screening agent of the 4,4-diarylbutadiene type.

Other characteristics, aspects and advantages of the invention will be seen from the detailed description which follows.

DETAILED DESCRIPTION OF BEST MODE AND SPECIFIC/PREFERRED EMBODIMENTS OF THE INVENTION

The polymers formulated in accordance with the invention are crosslinked or non-crosslinked homopolymers or copolymers containing at least the acrylamido-2-methylpropanesulfonic acid (AMPS) monomer, in free or alternatively partially or completely neutralized form.

Preferably, the AMPS polymers in accordance with the invention may be partially or completely neutralized with an inorganic base (sodium hydroxide, potassium hydroxide, aqueous ammonia) or an organic base such as mono-, di- or triethanolamine, an aminomethypropanediol, N-methylglucamine, basic amino acids such as arginine and lysine, and mixtures of these compounds. They are generally neutralized. The expression "neutralized" is understood to mean in the present invention polymers which are completely or practically completely neutralized, that is to say at least 90% neutralized.

These AMPS polymers according to the invention may be crosslinked or non-crosslinked.

When the polymers are crosslinked, the crosslinking agents may be selected from among the olefinically poly-unsaturated compounds commonly used for the crosslinking of polymers obtained by free-radical polymerization.

There may be mentioned, for example, as crosslinking agents, divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylol propane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of the sugar series, or other allyl or vinyl ethers of polyfunctional alcohols, and the allyl esters of phosphoric and/or vinylphosphonic acid derivatives, or mixtures of these compounds.

According to a preferred embodiment of the invention, the crosslinking agent is selected from methylenebisacrylamide, allyl methacrylate or trimethylolpropane triacrylate (TMPTA). The degree of crosslinking ranges in general from 0.01 mol % to 10 mol % and more particularly from 0.2 mol % to 2 mol % relative to the polymer.

The AMPS polymers in accordance with the invention may be water-soluble or water-dispersible. They are in this case:

either "homopolymers" containing only AMPS monomers and, if they are crosslinked, one or more crosslinking agents such as those defined above;

or copolymers obtained from AMPS and one or more hydrophilic or hydrophobic ethylenically unsaturated monomers and, if they are crosslinked, one or more crosslinking agents such as those defined above. When the said copolymers contain hydrophobic ethylenically unsaturated monomers, the latter do not contain a fatty chain and are preferably present in small quantities.

The expression "fatty chain" is understood to mean, for the purposes of the present invention, any hydrocarbon chain containing at least 7 carbon atoms.

The expression "water-soluble or water-dispersible" is understood to mean polymers which, when introduced into an aqueous phase at 25° C., at a concentration by mass equal to 1%, allow the obtaining of a macroscopically homogeneous and transparent solution, that is to say having a maximum light transmittance value, at a wavelength equal to 500 nm, through a sample 1 cm thick, of at least 60%, preferably of at least 70%.

The AMPS polymers in accordance with the invention may also be amphiphilic, namely that they contain both a hydrophilic part or moiety and a hydrophobic part or moiety containing at least one fatty chain.

Water-soluble or Water-dispersible Polymers:

When the polymers in accordance with the invention are water-soluble or water-dispersible (non-amphiphilic) copolymers, they are:

either "homopolymers" containing only AMPS monomers and, if they are crosslinked, one or more crosslinking agents;

or copolymers obtained from AMPS and one or more hydrophilic or hydrophobic ethylenically unsaturated monomers and, if they are crosslinked, one or more crosslinking agents. When the said copolymers contain hydrophobic ethylenically unsaturated monomers, the latter do not contain a fatty chain (number of carbon atoms not exceeding 6).

The "homopolymers" according to the invention are preferably crosslinked and neutralized, and they may be obtained according to the method of preparation comprising the following steps:

(a) the monomer such as AMPS in free form is dispersed or dissolved in a solution of tert-butanol or of water and tert-butanol;

(b) the solution or dispersion of monomer obtained in (a) is neutralized with one or more inorganic or organic bases, preferably aqueous ammonia $NH_3$, in a quantity which makes it possible to obtain a degree of neutralization of the sulfonic acid functional groups of the polymer ranging from 90% to 100%;

(c) the crosslinking monomer(s) is(are) added to the solution or dispersion obtained in (b);

(d) a conventional free-radical polymerization is carried out in the presence of free radical initiators at a temperature ranging from 10 to 150° C.; the polymer precipitating in the solution or the dispersion based on tert-butanol.

As polymers of this type, there may be mentioned, in particular, the crosslinked and neutralized 2-acrylamido-2-methylpropanesulfonic acid homopolymer marketed by Hoechst under the trademark "Hostacerin AMPS" (CTFA name: ammonium polyacryldimethyltauramide).

The water-soluble or water-dispersible AMPS copolymers according to the invention contain water-soluble, ethylenically unsaturated monomers, hydrophobic monomers or mixtures thereof.

The water-soluble comonomers may be ionic or nonionic.

Among the ionic water-soluble comonomers, there may be mentioned, for example the following compounds and their salts:

(meth)acrylic acid,
styrenesulfonic acid, vinylsulfonic acid and (meth)allylsulfonic acid, vinylphosphonic acid, maleic acid, itaconic acid, crotonic acid, dimethyldiallylammonium chloride, methylvinylimidazolium chloride, ethylenic carboxybetaines or sulfobetaines obtained for example by quaternization of ethylenically unsaturated monomers containing an amine functional group, with sodium salts of a carboxylic acid with an active halogen (e.g.,: chloroacetate) or with cyclic sulfones (e.g.,: propanesulfone), water-soluble vinyl monomers of the following formula (A):

(A)

in which $R_1$ is selected from H, —$CH_3$, —$C_2H_5$ or —$C_3H_7$ and $X_1$ is selected from the group consisting of:

alkyl oxides of the —$OR_2$ type wherein $R_2$ is a saturated or unsaturated, linear or branched hydrocarbon radical having from 1 to 6 carbon atoms, substituted with at least one sulfonic group (—$SO_3^-$) and/or sulfate group (—$SO_4^-$) and/or phosphate group (—$PO_4H_2^-$) and/or quaternary ammonium group (—$N^+R_3R_4R_5$) in which $R_3$, $R_4$ and $R_5$, which may be identical or different, are each a saturated or unsaturated, linear or branched hydrocarbon radical having 1 to 6 carbon atoms, provided that the sum of the carbon atoms of $R_1+R_2+R_3+R_4$ does not exceed 6. The radical $R_1$ is optionally substituted with a halogen atom (iodine, bromine, chlorine, fluorine); a hydroxyl (—OH); an ether (—O—), a primary amine (—$NH_2$); a secondary amine (—$NHR_6$), a tertiary amine (—$NR_6R_7$) in which $R_6$ and $R_7$, which may be identical or different, are each a saturated or unsaturated, linear or branched hydrocarbon radical having 1 to 6 carbon atoms, provided that the sum of the carbon atoms of $R_2+R_6+R_7$ does not exceed 6. Exemplary is quaternized dimethylaminoethyl methacrylate (DAMEMA).

—$NH_2$, —$NHR_8$ and —$NR_8R_9$ groups in which $R_8$ and $R_9$, which may be identical or different, are each a saturated or unsaturated, linear or branched hydrocarbon radical having 1 to 6 carbon atoms, provided that the total number of carbon atoms of $R_8+R_9$ does not exceed 6, the said $R_8$ and/or $R_9$ being substituted with at least one sulfonic group (—$SO_3^-$) and/or sulfate group (—$SO_4^-$) and/or phosphate group (—$PO_4H_2^-$) and/or quaternary amine group (—$N^+R_{10}R_{11}R_{12}$) in which $R_{10}$, $R_{11}$ and $R_{12}$, which may be identical or different, are each a saturated or unsaturated, linear or branched hydrocarbon radical having 1 to 6 carbon atoms, provided that the number of carbon atoms of $R_8+R_9+R_{10}+R_{11}+R_{12}$ does not exceed 6. The radicals $R_8$ and/or $R_9$ are optionally substituted with a halogen atom (iodine, bromine, chlorine, fluorine); a hydroxyl group (—OH); an ether group (—O—), a primary amine group (—$NH_2$); a secondary amine group (—$NHR_{13}$), a tertiary amine group (—$NR_{13}R_{14}$) in which $R_{13}$ and $R_{14}$, which may be identical or different, are each a saturated or unsaturated, linear or branched hydrocarbon radical having 1 to 6 carbon atoms, provided that the sum of the carbon atoms of $R_8+R_9+R_{13}+R_{14}$ does not exceed 6. Exemplary is (meth) acrylamidopropyltrimethylammonium chloride (APTAC and MAPTAC).

Among the nonionic water-soluble comonomers, there may be mentioned, for example:

(meth)acrylamide,

N-vinylacetamide and N-methyl-N-vinylacetamide,

N-vinylformamide and N-methyl-N-vinylformamide, maleic anhydride, vinylamine,

N-vinyllactams containing a cyclic alkyl group having from 4 to 9 carbon atoms, such as N-vinylpyrrolidone, N-butyrolactam and N-vinylcaprolactam, vinyl alcohol of formula $CH_2$=CHOH, water-soluble vinyl monomers of the following formula (B):

(B)

in which $R_{15}$ is selected from H, —$CH_3$, —$C_2H_5$ or —$C_3H_7$ and $X_2$ is selected from the group consisting of:

alkyl oxides of the —$OR_{16}$ type wherein $R_{16}$ is a saturated or unsaturated, linear or branched hydrocarbon radical having from 1 to 6 carbons, optionally substituted with a halogen atom (iodine, bromine, chlorine, fluorine); a hydroxyl group (—OH); an ether group (—O—), a primary amine group (—$NH_2$); a secondary amine group (—$NHR_{17}$), a tertiary amine group (—$NR_{17}R_{18}$) in which $R_{17}$ and $R_{18}$, which may be identical or different, are each a saturated or unsaturated, linear or branched hydrocarbon radical having 1 to 6 carbon atoms, provided that the sum of the carbon atoms of $R_{16}+R_{17}+R_{18}$ does not exceed 6. Exemplary is glycidyl (meth)acrylate, hydroxyethyl methacrylate, and ethylene glycol, diethylene glycol or polyalkylene glycol (meth)acrylates;

—$NH_2$, —$NHR_{19}$ and —$NR_{19}R_{20}$ groups in which $R_{19}$ and $R_{20}$, which may be identical or different, are each a saturated or unsaturated, linear or branched hydrocarbon radical having 1 to 6 carbon atoms, provided that the total number of carbon atoms of $R_{19}+R_{20}$ does not exceed 6, the said $R_{19}$ and $R_{20}$ being optionally substituted with a halogen atom (iodine, bromine, chlorine, fluorine); a hydroxyl group (—OH); an ether group (—O—); a primary amine group (—$NH_2$); a secondary amine group (—$NHR_{21}$), a tertiary amine group (—$NR_{21}R_{22}$) in which $R_{21}$ and $R_{22}$, which may be identical or different, are each a saturated or unsaturated, linear or branched hydrocarbon radical having 1 to 6 carbon atoms, provided that the sum of the carbon atoms of $R_{19}+R_{20}+R_{21}+R_{22}$ does not exceed 6. Exemplary is dimethylaminoethylmethacrylamide.

Among the hydrophobic comonomers with no fatty chain, there may be mentioned, for example:

styrene and its derivatives such as 4-butylstyrene, alpha-methylstyrene and vinyltoluene, vinyl acetate of formula $CH_2$=CH—$OCOCH_3$, vinyl ethers of formula $CH_2$=CHOR in which R is a saturated or unsaturated, linear or branched hydrocarbon radical having from 1 to 6 carbons, acrylonitrile, caprolactone, vinyl chloride and vinylidene chloride,
silicone derivatives, after polymerization providing silicone polymers such as methacryloxypropyltris(trimethylsiloxy)silane and silicone methacrylamides,
hydrophobic vinyl monomers of the following formula (C):

in which $R_{23}$ is selected from H, $-CH_3$, $-C_2H_5$ or $-C_3H_7$ and $X_3$ is selected from the group consisting of:
  alkyl oxides of the $-OR_{24}$ type where $R_{24}$ is a saturated or unsaturated, linear or branched hydrocarbon radical having from 1 to 6 carbon atoms;
  $-NH_2$, $-NHR_{25}$ and $-NR_{25}R_{26}$ groups in which $R_{25}$ and $R_{26}$, which may be identical or different, are each a saturated or unsaturated, linear or branched hydrocarbon radicals having 1 to 6 carbon atoms, provided that the total number of carbon atoms of $R_{25}+R_{26}$ does not exceed 6. Exemplary are methyl methacrylate, ethyl methacrylate, n-butyl(meth)acrylate, tert-butyl(meth)acrylate, cyclohexyl acrylate, isobornyl acrylate and 2-ethylhexyl acrylate.

The water-soluble or water-dispersible AMPS polymers of the invention preferably have a molar mass ranging from 50,000 g/mol to 10,000,000 g/mol, preferably from 80,000 g/mol to 8,000,000 g/mol, and more preferably still from 100,000 g/mol to 7,000,000 g/mol.

As water-soluble or water-dispersible copolymers obtained from AMPS and ethylenically unsaturated water-soluble monomers, there may be mentioned, for example, those obtained from AMPS and acrylamide or methacrylamide, such as, for example, the acrylamide/sodium acrylamido-2-methylpropanesulfonate crosslinked copolymer as an emulsion in $C_{13}$–$C_{14}$ isoparaffin and laureth-7 (CTFA name: Polyacrylamide/$C_{13}$–$C_{14}$ isoparaffin/laureth-7) marketed under the name SEPIGEL 305 or acrylamide/sodium acrylamido-2-methylpropanesulfonate crosslinked copolymer as an invert emulsion at 40% in isohexadecane and polysorbate-80 (CTFA name: Acrylamide/Sodium Acryloyldimethyltaurate/isohexadecane/polysorbate-80) marketed under the name SIMULGEL 600 by SEPPIC. There may also be mentioned the copolymers of AMPS and vinylpyrrolidone or vinylformamide, such as the products ammonium acryloyldimethyltaurate/VP copolymer (INCI name) marketed under the name ARISTOFLEX AVC by CLARIANT. There may also be mentioned the copolymers of AMPS and sodium acrylate, such as for example AMPS/sodium acrylate crosslinked copolymer as an invert emulsion in a water/isohexadecane/sorbitan oleate mixture (CTFA name: Acrylamide/Sodium Acryloyldimethyltaurate/Isohexadecane/polysorbate-80) marketed under the name SIMULGEL EG by SEPPIC. There may also be mentioned the copolymers of AMPS and hydroxyethyl acrylate, such as for example AMPS/hydroxyethyl acrylate crosslinked copolymer as an invert emulsion in a polysorbate 60/squalane mixture (INCI name: Hydroxyethyl acrylate/Sodium Acryloyldimethyltaurate copolymer (and) squalane (and) polysorbate 60) marketed under the name SIMULGEL NS by SEPPIC.

Amphiphilic AMPS Polymers:

The amphiphilic AMPS polymers in accordance with the invention contain both a hydrophilic part or moiety and a hydrophobic part or moiety containing at least one fatty chain.

The fatty chain present in the polymers of the invention preferably contain from 7 to 30 carbon atoms, more preferably from 7 to 22 carbon atoms and more preferably still from 7 to 18 atoms and more particularly from 12 to 18 carbon atoms.

The amphiphilic polymers in accordance with the invention have in general a weight-average molecular weight ranging from 50,000 to 10,000,000, more preferably from 100,000 to 8,000,000 and more preferably still from 100,000 to 7,000,000.

The amphiphilic AMPS polymers according to the invention may be crosslinked or non-crosslinked. The crosslinking agents may be selected from among those mentioned above. There may be used more particularly methylenebisacrylamide, allyl methacrylate or trimethylolpropane triacrylate (TMPTA). The degree of crosslinking preferably varies from 0.01 mol % to 10 mol %, and more particularly from 0.2 mol % to 2 mol % relative to the polymer.

The amphiphilic AMPS polymers in accordance with the invention may be selected in particular from among random amphiphilic AMPS polymers modified by reaction with a $C_6$–$C_{22}$ n-monoalkylamine or di-n-alkylamine such as those described in WO 00/31154. These polymers may also contain other ethylenically unsaturated hydrophilic monomers selected, for example, from among acrylic acid, methacrylic acid or their β-substituted alkyl derivatives or their esters obtained with mono- or polyalkylene glycols, acrylamide, methacrylamide, vinylpyrrolidone, itaconic acid, maleic acid or mixtures thereof.

The preferred polymers of the invention are selected from among the amphiphilic polymers of AMPS and at least one ethylenically unsaturated monomer containing at least one hydrophobic part or moiety having from 7 to 30 carbon atoms and more preferably from 7 to 22 carbon atoms and even more preferably still from 7 to 18 carbon atoms and more particularly from 12 to 18 carbon atoms. This hydrophobic part or moiety may be a saturated or unsaturated, linear alkyl radical (for example n-octyl, n-decyl, n-hexadecyl, n-dodecyl, oleyl), branched radical (for example isostearyl) or cyclic radical (for example cyclododecane or adamantane).

These same polymers may further contain one or more ethylenically unsaturated hydrophilic comonomers such as acrylic acid, methacrylic acid or their β-substituted alkyl derivatives or their esters obtained with mono- or polyalkylene glycols, acrylamide, methacrylamide, vinylpyrrolidone, itaconic acid or maleic acid.

These same polymers may further contain one or more ethylenically unsaturated hydrophobic comonomers comprising, for example:
  a $C_7$–$C_{18}$ fluorinated or alkylfluorinated radical (for example the group of formula $-(CH_2)_2-(CF_2)_9-CF_3$),
  a cholesteryl radical or a radical derived from cholesterol (for example cholesteryl hexanoate),
  an aromatic polycyclic group such as naphthalene or pyrene,
  a silicone or alkylsilcone or alternatively alkylfluorosilicone radical.

These copolymers are described in particular in EP-A-750,899, in U.S. Pat. No. 5,089,578 and in the following publications by Yotaro Morishima:

"Self-assembling amphiphilic polyelectrolytes and their nanostructures—Chinese Journal of Polymer Science, Vol. 18, No. 40, (2000), 323–336;

"Micelle formation of random copolymers of sodium 2-(acrylamido-2-methylpropanesulfonate and a non-ionic surfactant macromonomer in water as studied by fluorescence and dynamic light scattering—Macromolecules 2000, Vol. 33, No. 10-3694–3704";

"Solution properties of miscelle networks formed by non-ionic moieties covalently bound to an polyelectrolyte: salt effects on rheological behaviour—Langmuir, 2000, Vol. 16, No. 12, 5324–5332";

"Stimuli response amphiphilic copolymers of sodium 2-(acrylamido)-2-methylpropanesulfonate and associative macromonomers—Polym. Preprint, Div. Polym. Chem. 1999, 40(2), 220–221".

They are also described in (CLARIANT): EP-1,069,142, WO 02/44224, WO 02/44225, WO 02/44227, WO 02/44229, WO 02/44230, WO 02/44231, WO 02/44267, WO 02/44268, WO 02/44269, WO 02/44270, WO 02/44271, WO 02/43677, WO 02/43686, WO 02/43687, WO 02/43688, WO 02/43689.

The ethylenically unsaturated hydrophobic monomers of the invention are preferably selected from among the acrylates and acrylamides of the following formula (1):

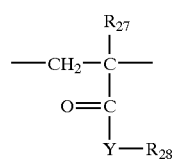

(1)

in which $R_{27}$ is a hydrogen atom, a linear or branched $C_1$–$C_6$ alkyl radical (preferably methyl); Y is O or NH; $R_{28}$ is a hydrophobic radical containing a fatty chain having from 7 to 22 carbon atoms, and preferably 7 to 18, and more particularly from 12 to 18 carbon atoms.

The hydrophobic radical $R_{28}$ is preferably selected from among the saturated or unsaturated, linear $C_7$–$C_{18}$ alkyl radicals (for example n-octyl, n-decyl, n-hexadecyl, n-dodecyl, oleyl), branched radicals (for example isostearyl) or cyclic radicals (for example cyclododecane or adamantane); perfluorinated $C_7$–$C_{18}$ alkyl radicals (for example the group of formula —(CH$_2$)$_2$—(CF$_2$)$_9$—CF$_3$); the cholesteryl radical or a cholesterol ester such as cholesteryl hexanoate; aromatic polycyclic groups such as naphthalene or pyrene. Among these radicals, the linear and branched alkyl radicals are more particularly preferred.

According to a particularly preferred embodiment of the invention, the hydrophobic radical $R_{28}$ further contains at least one alkylene oxide unit and preferably a polyoxyalkylenated chain. The preferably polyoxyalkylenated chain comprises ethylene oxide units and/or propylene oxide units and more particularly still solely comprises ethylene oxide units. The number of moles of oxyalkylenated units varies in general from 1 to 30 mol and more preferably from 1 to 25 mol and more preferably still from 3 to 20 mol.

Among these polymers, there may be mentioned:

neutralized or non-neutralized, crosslinked or non-crosslinked copolymers containing from 15% to 60% by weight of AMPS units and from 40% to 85% by weight of (C$_8$–C$_{16}$)alkyl (meth)acrylamide units or (C$_8$–C$_{16}$)alkyl (meth)acrylate units relative to the polymer, such as those described in EP-A-750,899;

terpolymers containing from 10 to 90 mol % of acrylamide units, from 0.1 to 10 mol % of AMPS units and from 5 to 80 mol % of n-(C$_6$–C$_{18}$)alkyl acrylamide units, relative to the polymer, such as those described in U.S. Pat. No. 5,089,578.

As amphiphilic polymers, there may also be mentioned the copolymers of completely neutralized AMPS and of n-dodecyl, n-hexadecyl and/or n-octadecyl methacrylate, and the copolymers of AMPS and n-dodedcyl methacrylamide, which are non-crosslinked and crosslinked.

There may be mentioned, more particularly, the crosslinked or non-crosslinked amphiphilic copolymers comprising:

(a) 2-acrylamido-2-methylpropanesulfonic acid (AMPS) units of the following formula (2):

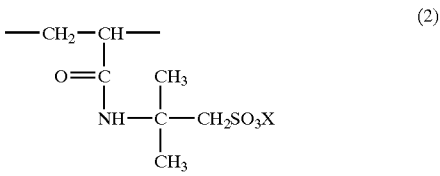

(2)

in which $X^+$ is a proton, an alkali metal cation, an alkaline earth metal cation or the ammonium ion;

(b) and of units of the following formula (3):

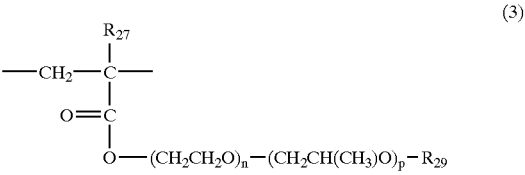

(3)

in which n and p, which may be identical or different, denote a number of moles and varies from 0 to 30, preferably from 1 to 25 and more preferably from 3 to 20, provided that n+p is less than or equal to 30, preferably less than 25 and better still less than 20; $R_{27}$ has the same meaning indicated above in formula (1) and $R_{29}$ is a linear or branched alkyl radical containing m carbon atoms ranging from 7 to 22, preferably from 7 to 18 carbon atoms and better still from 12 to 18 carbon atoms.

In formula (2), the cation $X^+$ more particularly is sodium or ammonium.

Among the monomers of formula (3), there may be mentioned:

esters of (meth)acrylic acid and a polyoxyethylenated C$_{10}$–C$_{18}$ fatty alcohol containing 8 EO such as the product GENAPOL C-080 sold by CLARIANT;

esters of (meth)acrylic acid and a polyoxyethylenated C$_{11}$ fatty oxoalcohol containing 8 EO such as the product GENAPOL UD-080 sold by CLARIANT;

esters of (meth)acrylic acid and a polyoxyethylenated C$_{12}$–C$_{14}$ fatty alcohol containing 7 EO such as the product GENAPOL LA-070 sold by CLARIANT;

esters of (meth)acrylic acid and a polyoxyethylenated C$_{12}$–C$_{14}$ fatty alcohol containing 11 EO such as the product GENAPOL LA-110 sold by CLARIANT;

esters of (meth)acrylic acid and a polyoxyethylenated C$_{16}$–C$_{18}$ fatty alcohol containing 8 EO such as the product GENAPOL T-080 sold by CLARIANT;

esters of (meth)acrylic acid and a polyoxyethylenated C$_{16}$–C$_{18}$ fatty alcohol containing 15 EO such as the product GENAPOL T-150 sold by CLARIANT;

esters of (meth)acrylic acid and a polyoxyethylenated C$_{16}$–C$_{18}$ fatty alcohol containing 11 EO such as the product GENAPOL T-110 sold by CLARIANT;

esters of (meth)acrylic acid and a polyoxyethylenated $C_{16}$–$C_{18}$ fatty alcohol containing 20 EO such as the product GENAPOL T-200 sold by CLARIANT;

esters of (meth)acrylic acid and a polyoxyethylenated $C_{16}$–$C_{18}$ fatty alcohol containing 25 EO such as the product GENAPOL T-250 sold by CLARIANT;

esters of (meth)acrylic acid and a polyoxyethylenated $C_{18}$–$C_{22}$ fatty alcohol containing 25 EO and/or a polyoxyethylenated $C_{16}$–$C_{18}$ fatty isoalcohol containing 25 EO.

There will more particularly be selected:

(i) those which are non-crosslinked, for which p=0, n=7 or 25, $R_{27}$ is methyl and $R_{29}$ is a mixture of $C_{12}$–$C_{14}$ or $C_{16}$–$C_{18}$ alkyl, (ii) those which are crosslinked, for which p=0, n=8 or 25, $R_{27}$ is methyl and $R_{29}$ represents a mixture of $C_{16}$–$C_{18}$ alkyl.

These polymers are described and synthesized in EP-1, 069,142. These particular amphiphilic polymers may be obtained according to conventional free-radical polymerization methods in the presence of one or more initiators such as for example azobisisobutyronitrile (AIBN), azobisdimethylvaleronitrile, 2,2-azobis[2-amidinopropane] hydrochloride (ABAH=2,2-azo-bis-[2-aminopropane] hydrochloride), organic peroxides such as dilauryl peroxide, benzoyl peroxide, tert-butyl hydroperoxide, and the like, inorganic peroxide compounds such as potassium or ammonium persulfate, or $H_2O_2$ optionally in the presence of reducing agents.

These amphiphilic polymers may be obtained in particular by free-radical polymerization in a tert-butanol medium in which they precipitate. Using polymerization by precipitation in tert-butanol, it is possible to obtain a distribution of the size of the polymer particles which is particularly favorable for its uses.

The reaction may be performed at a temperature of between 0 and 150° C., preferably between 10 and 100° C., or at atmospheric pressure or under reduced pressure. It may also be carried out under an inert atmosphere, preferably under nitrogen.

The polymers in accordance with the invention are preferably partially or completely neutralized with an inorganic or organic base such as those described above.

The mol % concentration of the units of formula (2) and of the units of formula (3) in the amphiphilic polymers according to the invention varies according to the desired cosmetic application, the nature of the emulsion (oil-in-water or water-in-oil) and the desired rheological properties of the formulation. They may vary between 0.1 and 99.9 mol %.

The scarcely hydrophobic amphiphilic AMPS polymers according to the invention will be more appropriate for thickening and/or stabilizing the oil-in-water emulsions. The molar proportion of units of formula (3) will preferably vary from 0.1% to 50%, more particularly from 1% to 25% and more particularly still from 3% to 10%.

The more hydrophobic amphiphilic AMPS polymers according to the invention will be more appropriate for thickening and/or stabilizing the water-in-oil emulsions. The molar proportion of units of formula (3) will preferably vary from 50.1% to 99.9%, more particularly from 60% to 95% and more particularly still from 65% to 90%.

The distribution of the monomers in the polymers of the invention may be for example alternating, block (including multiblock) or of any type.

The AMPS polymers in accordance with the invention are generally present in quantities as active material ranging from 0.01% to 20% by weight, more preferably from 0.1% to 10% by weight, still more preferably from 0.1% to 5% by weight and more particularly still from 0.5% to 2% by weight relative to the total weight of the composition.

The 4,4-diarylbutadiene compounds in accordance with the invention are preferably selected from among those corresponding to the following formula (I):

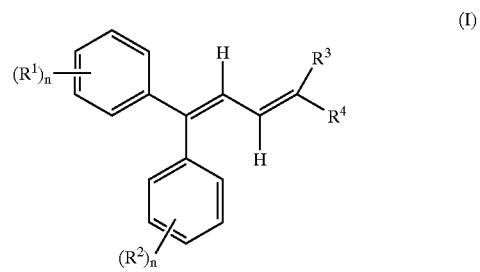

in which the diene system is of the Z,Z; Z,E; E,Z or E,E configuration or mixtures of the said configurations, and wherein:

$R^1$ and $R^2$, which may be identical or different, are each hydrogen, a $C_1$–$C_{20}$ alkyl radical, a $C_2$–$C_{10}$ alkenyl radical, a $C_1$–$C_{12}$ alkoxy radical, a $C_3$–$C_{10}$ cycloalkyl radical, a $C_3$–$C_{10}$ cycloalkenyl radical, a $C_1$–$C_{20}$ alkoxycarbonyl radical, a $C_1$–$C_{12}$ monoalkylamino radical, a $C_1$–$C_{12}$ dialkylamino radical, an aryl radical, a heteroaryl radical or a water-solubilizing substituent selected from among a carboxylate residue, a sulfonate residue or an ammonium residue;

$R^3$ is a group $COOR^5$, $COR^5$, $CONR^5R^6$, $CN$, $O=S(-R^5)=O$, $O=S(-OR^5)=O$, $R^7O-P-(-OR^8)=O$, a $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ cycloalkenyl radical, a $C_7$–$C_{10}$ bicycloalkenyl radical, an optionally substituted $C_6$–$C_{18}$ aryl radical, an optionally substituted $C_3$–$C_7$ heteroaryl radical;

$R^4$ is a group $COOR^6$, $COR^6$, $CONR^5R^6$, $CN$, $O=S(-R^6)=O$, $O=S(-OR^6)=O$, $R^7O-P-(-OR^8)=O$, a $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ cycloalkenyl radical, a $C_7$–$C_{10}$ bicycloalkenyl radical, an optionally substituted $C_6$–$C_{18}$ aryl radical, an optionally substituted $C_3$–$C_7$ heteroaryl radical;

the radicals $R^5$ to $R^8$, which may be identical or different, are each hydrogen, a $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ bicycloalkenyl radical, a $C_7$–$C_{10}$ cycloalkenyl radical, an optionally substituted aryl radical, an optionally substituted heteroaryl radical; and n ranges from 1 to 3; with the proviso that the radicals $R^3$ to $R^8$ can together form, with the carbon atoms from which they depend, a $C_5$–$C_6$ ring which may be fused.

As $C_1$–$C_{20}$ alkyl radicals, there may be mentioned, for example: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

As $C_2$–$C_{10}$ alkenyl groups, there may be mentioned, for example: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl, n-decenyl.

As $C_1$–$C_{12}$ alkoxy radicals, there may be mentioned: methoxy, n-propxy, 1-methylpropoxy, 1-methylethoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy, 2-ethylhexoxy.

As $C_1$–$C_{20}$ alkoxycarbonyl radicals, there may be mentioned esters of $C_1$–$C_{20}$ alcohols.

As $C_1$–$C_{12}$ monoalkylamino or dialkylamino radicals, there may be mentioned those in which the alkyl radical(s) is(are) selected from among methyl, n-propyl, 2-methylpropyl, 1,1-dimethylethyl, hexyl, heptyl, 2-ethylhexyl, isopropyl, 1-methylpropyl, n-pentyl, 3-methylbutyl, 2,2-dimethylpropyl, 1-methyl-1-ethylpropyl, octyl.

As $C_3$–$C_{10}$ cycloalkyl radicals, there may be mentioned, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

As $C_3$–$C_{10}$ cycloalkenyl radicals having one or more double bonds, there may be mentioned: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctetraenyl, cyclononenyl or cyclodecenyl.

The cycloalkyl or cycloalkenyl radicals may comprise one or more substituents (preferably from 1 to 3) selected, for example, from among halogens such as chlorine, fluorine or bromine; cyano; nitro; amino; $C_1$–$C_4$ alkylamino; $C_1$–$C_4$ dialkylamino; $C_1$–$C_4$ alkyl; $C_1$–$C_4$ alkoxy; hydroxyl; they may also comprise from 1 to 3 heteroatoms such as sulfur, oxygen or nitrogen whose free valencies may be saturated with a hydrogen or a $C_1$–$C_4$ alkyl radical.

The bicycloalkyl or bicycloalkenyl groups are selected, for example, from among bicyclic terpenes such as pinane, bornane, pinene or camphor or adamantane derivatives.

The aryl groups are preferably selected from phenyl or naphthyl rings, which may comprise one or more substituents (preferably from 1 to 3) selected for example from halogen such as chlorine, fluorine or bromine; cyano; nitro; amino; $C_1$–$C_4$ alkylamino; $C_1$–$C_4$ dialkylamino; $C_1$–$C_4$ alkyl; $C_1$–$C_4$ alkoxy; hydroxyl. Phenyl, methoxyphenyl, naphthyl and thienyl are more particularly preferred.

The heteroaryl groups comprise in general one or more heteroatoms selected from among sulfur, oxygen or nitrogen.

The water-solubilizing groups are for example carboxyl and sulfoxy residues, and more particular their salts with physiologically acceptable cations such as alkali metal salts or trialkylammonium salts such as tri(hydroxyalkyl) ammonium or 2-methylpropan-1-ol-2-ammonium salts. There may also be mentioned ammonium groups such as alkylammoniums and their salified forms with physiologically acceptable anions.

The compounds of formula (I) are known per se and their structures and their syntheses are described in DE-1-9,755,649, EP-916,335, EP-1,133,980 and EP-1,133,981.

By way of example of a compound of formula (I), the following are representative:

(compound a)

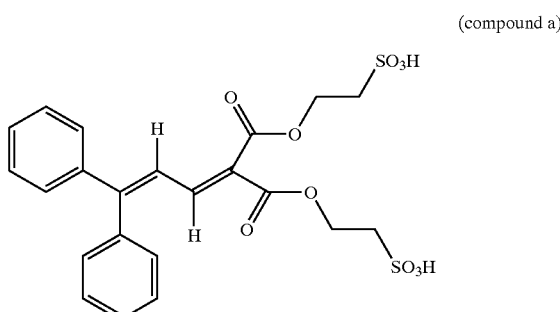

(compound b)

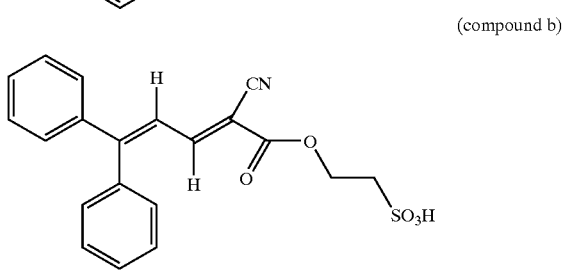

(compound c)

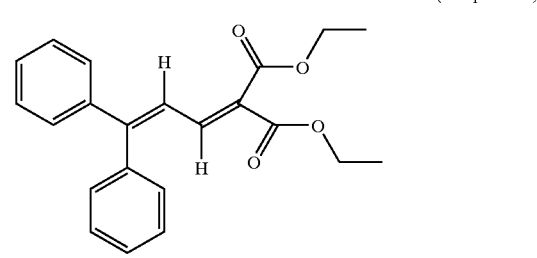

(compound d)

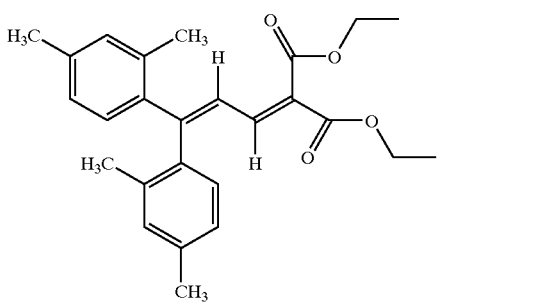

(compound e)

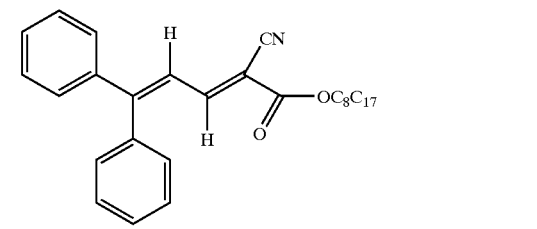

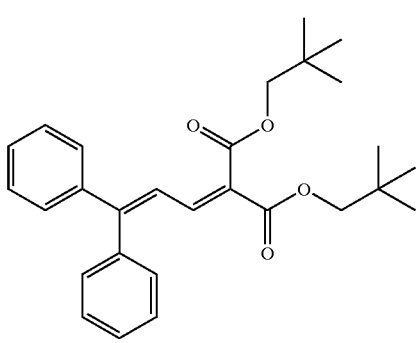

(compound f)

The preferred compounds of formula (I) are those in which:

n=1 or 2;

$R^1$ and $R^2$, which may be identical or different, are each hydrogen, a $C_1$–$C_{20}$ alkyl radical, a $C_1$–$C_{12}$ alkoxy radical, a $C_1$–$C_{12}$ monoalkylamino radical, a $C_1$–$C_{12}$ dialkylamino radical, a water-solubilizing substituent selected from among a carboxylate group, a sulfonate group or an ammonium residue;

$R^3$ is a group $COOR^5$, $COR^5$, $CONR^5R^6$, a $C_1$–$C_{20}$ alkyl radical, a $C_3$–$C_{10}$ cycloalkyl radical, a $C_3$–$C_{10}$ cycloalkenyl radical, a $C_7$–$C_{10}$ bicycloalkyl radical, optionally substituted phenyl, naphthyl or thienyl;

$R^4$ is a group $COOR^6$, $COR^6$, $CONR^5R^6$, a $C_1$–$C_{20}$ alkyl radical, a $C_3$–$C_6$ cycloalkyl radical, a $C_3$–$C_{10}$ cycloalkenyl radical, a $C_7$–$C_{10}$ bicycloalkyl radical, optionally substituted phenyl, naphthyl or thienyl;

the radicals $R^5$ and $R^6$, which may be identical or different, are each hydrogen, a $C_1$–$C_{12}$ alkyl radical, a $C_3$–$C_{10}$ cycloalkyl radical, a $C_3$–$C_{10}$ cycloalkenyl radical, a $C_7$–$C_{10}$ bicycloalkyl radical, a $C_3$–$C_{10}$ bicycloalkenyl radical, optionally substituted phenyl or naphthyl.

Among these compounds, there are more particularly preferred those in which:

$R^1$ and $R^2$, which may be identical or different, are each hydrogen, a $C_1$–$C_{20}$ alkyl radical, a $C_1$–$C_{20}$ alkoxy radical, a water-solubilizing substituent selected from among a carboxylate group, a sulfonate group or an ammonium residue;

$R^3$ is a group $COOR^5$, $COR^5$, $CONR^5R^6$;

$R^4$ is a group $COOR^6$, $COR^6$, $CONR^5R^6$;

the radicals $R^5$ and $R^6$, which may be identical or different, are each hydrogen, a $C_1$–$C_{12}$ alkyl radical, a $C_3$–$C_6$ cycloalkyl radical, a $C_3$–$C_{10}$ cycloalkenyl radical, a $C_7$–$C_{10}$ bicycloalkyl radical, a $C_3$–$C_{10}$ bicycloalkenyl radical, optionally substituted phenyl or naphthyl.

According to a particularly preferred embodiment, the compounds of formula (I) are selected from among those of the following formula (I'):

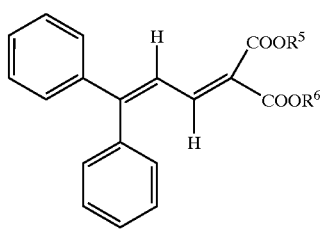

(I')

wherein the radicals $R^5$ and $R^6$, which may be identical or different, are each hydrogen, a $C_1$–$C_{20}$ alkyl radical, a $C_3$–$C_6$ cycloalkyl radical, a $C_3$–$C_{10}$ cycloalkenyl radical.

Among these compounds of formula (I'), there may be mentioned, more particularly, 1,1-dicarboxy(2,2'-dimethylpropyl)-4,4-diphenylbutadiene having the structure:

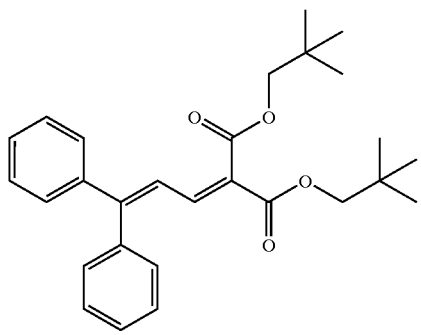

(compound f)

Another 4,4-diarylbutadiene family which may formulated into the emulsions according to the invention are those corresponding to the following formula (II):

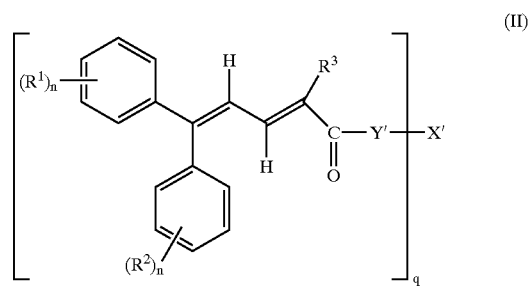

(II)

in which the diene system is of the Z,Z; Z,E; E,Z or E,E configuration or mixtures of the said configurations and wherein:

$R^1$, $R^2$, $R^3$ and n have the same meanings indicated in the preceding formula (I);

Y' is a group —O— or —$NR^9$—;

$R^9$ is hydrogen, a linear or branched $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ cycloalkenyl radical, a $C_7$–$C_{10}$ bicycloalkenyl radical, an aryl radical, a heteroaryl radical;

X' is a residue of a linear or branched, aliphatic or cycloaliphatic $C_2$–$C_{20}$ polyol comprising from 2 to 10 hydroxyl groups and having the valency q; with the proviso that the carbon chain of the said residue may be interrupted by one or more sulfur or oxygen atoms, one or more imine groups, one or more $C_1$–$C_4$ alkylimino groups;

q ranges from 2 to 10; and

X' is a $C_2$–$C_{20}$ polyol residue containing from 2 to 10 hydroxyl groups, and in particular:

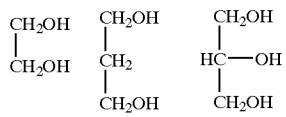

-continued

[Chemical structures of polyols including pentaerythritol, trimethylolethane, sorbitol, dipentaerythritol, and related compounds; a methylcyclohexane tetraol; rhamnose; a hexose; and a bis-piperidinyl diamine compound with hydroxyl groups]

The more preferred compounds of formula (II) are those in which:

$R^1$ and $R^2$, which may be identical or different, are each hydrogen, a $C_1$–$C_{12}$ alkyl radical, a $C_1$–$C_8$ alkoxy radical, a water-solubilizing substituent selected from among a carboxylate group, a sulfonate group or an ammonium residue;

$R^3$ is a group $COOR^5$, $CONR^5R^6$, CN, a $C_3$–$C_{10}$ cycloalkyl radical, a $C_7$–$C_{10}$ bicycloalkyl radical;

$R^5$ and $R^6$, which may be identical or different, are each a linear or branched $C_1$–$C_{20}$ alkyl radical, a $C_3$–$C_{10}$ cycloalkyl radical, a $C_7$–$C_{10}$ bicycloalkyl radical, optionally substituted naphthyl or phenyl;

X' is a $C_2$–$C_{20}$ polyol residue comprising from 2 to 6 hydroxyl groups and more particularly from 2 to 4.

The even more preferred compounds of formula (II) are those in which:

X' is an ethanol or pentaerythritol residue.

The even more particularly preferred compounds of formula (II) are selected from among:

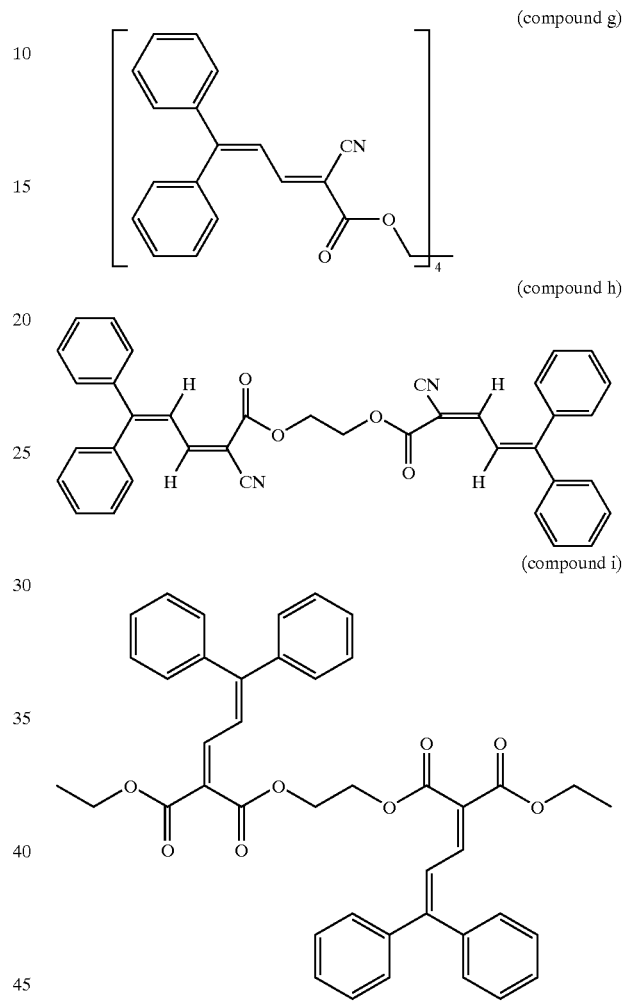

(compound g)

(compound h)

(compound i)

The compounds of formula (II) as defined above are known per se and their structures and their syntheses are described in EP-A-1,008,586.

The 4,4-diarylbutadiene compounds are preferably present in the composition in proportions ranging from 0.1% to 20% by weight, more preferably from 1% to 10% by weight relative to the total weight of the composition.

The compositions according to the invention may be provided in any of the galenic forms containing a fatty phase and an aqueous phase which are conventionally used for topical application and in particular in the form of dispersions of the lotion or serum type, emulsions having a liquid or semi-liquid consistency of the milk type, which are obtained by dispersing a fatty phase in an aqueous phase (O/W) or conversely (W/O), suspensions or emulsions having a soft, semi-solid or solid consistency of the cream or gel type, or alternatively multiple emulsions (W/O/W or O/W/O), microemulsions, vesicular dispersions of the ionic and/or nonionic type, or wax/aqueous phase dispersions. These compositions are prepared according to the customary methods.

According to a particular embodiment of the invention, the oil-in-water or water-in-oil emulsions prepared with the AMPS polymers and/or copolymers according to the invention may contain only 1% by weight or less, and may even be free of emulsifying surfactants, while being stable during storage.

The nature of the fatty phase entering into the composition of the emulsions according to the invention is not critical and it may thus comprise all the compounds which are already known in general as being suitable for the manufacture of emulsions. In particular, these compounds may be selected, alone or as mixtures, from various fatty substances, oils of plant, animal or mineral origin, natural or synthetic waxes, and the like.

Among the oils which may be formulated into the composition of the fatty phase, there may be mentioned in particular:

- mineral oils such as paraffin oil and liquid paraffin,
- oils of animal origin, such as perhydrosqualene,
- oils of plant origin, such as sweet almond oil, avocado oil, castor oil, olive oil, jojoba oil, sesame oil, groundnut oil, grape seed oil, rapeseed oil, copra oil, hazelnut oil, shea butter, palm oil, apricot kernel oil, calophyllum oil, rice bran oil, maize germ oil, wheat germ oil, soya bean oil, sunflower oil, evening primrose oil, safflower oil, passion flower oil and rye oil,
- synthetic oils, such as purcellin oil, esters, such as for example butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid such as isopropyl lanolate, isocetyl lanolate, isoparaffins and poly-α-olefins.

As other oils which can be formulated into the emulsions according to the invention, there may also be mentioned C12–C15 fatty alcohol benzoates (Finsolv TN from FINETEX), ethers, lipophilic amino acid derivatives such as isopropyl N-lauroylsarcosinate (Eldew SL-205 from Ajinomoto), fatty alcohols such as lauryl, cetyl, myristyl, stearyl, palmityl or oleyl alcohol and 2-octyldodecanol, acetylglycerides, octanoates and decanoates of alcohols and polyalcohols such as those of glycol and of glycerol, ricinoleates of alcohols and polyalcohols such as those of cetyl, fatty acid triglycerides such as caprylic/capric triglycerides, C10–C18 saturated fatty acid triglycerides, fluorinated and perfluorinated oils, lanolin, hydrogenated lanolin, acetylated lanolin and finally volatile or nonvolatile silicone oils.

Of course, the fatty phase may also contain one or more conventional lipophilic cosmetic adjuvants, such as for example waxes, lipophilic gelling agents, surfactants, organic or inorganic particles, and in particular those which are already customarily used in the manufacture and production of anti-sun cosmetic compositions.

Conventionally, the dispersive aqueous phase may comprise water, or a mixture of water and polyhydric alcohol(s) such as for example glycerol, butylene glycol, propylene glycol and sorbitol, or alternatively a mixture of water and water-soluble lower alcohol(s) such as ethanol, isopropanol or butanol (aqueous-alcoholic solution).

The compositions in accordance with the invention may further comprise other additional organic or inorganic UV-screening agents which are active in UV-A and/or UV-B, which are water-soluble or fat-soluble or alternatively insoluble in the commonly-used cosmetic solvents.

The additional organic screening agents are selected in particular from among anthranilates; cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243 and EP-944,624; benzophenone derivatives; β,β-diphenyl acrylate derivatives; benzotriazole derivatives; benzalmalonate derivatives; benzimidazole derivatives; imidazolines; p-aminobenzoic acid (PABA) derivatives, benzoxazol derivatives as described in EP-0-832,642, E-1,027,883, E-1, 300,137 and DE-1-0,162,844; bis-benzoazolyl derivatives as described in EP-669,323 and U.S. Pat. No. 2,463,264; p-aminobenzoic acid (PABA) derivatives; methylenebis (hydroxyphenylbenzotriazole) derivatives as described in U.S. Pat. Nos. 5,237,071, 5,166,355, GB-2,303,549, DE-197-26-184 and EP-893,119; screening polymers and screening silicones such as those described in particular in WO 93/04665; dimers derived from α-alkylstyrene such as those described in DE-198-55-649 and mixtures thereof.

As examples of organic screening agents which are active in the UV-A and/or UV-B regions, there may be mentioned those designated below under their INCI names:

para-Aminobenzoic Acid Derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF, Salicylic Derivatives:
Homosalate sold under the name "Eusolex HMS" by Rona/EM Industries,
Ethylhexyl Salicylate sold under the name "NEO HELIOPAN OS" by Haarmann and REIMER,
Dipropyleneglycol Salicylate sold under the name "DIPSAL" by SCHER,
TEA Salicylate, sold under the name "NEO HELIOPAN TS" by Haarmann and REIMER, Dibenzoylmethane Derivatives:
Butyl Methoxydibenzoylmethane sold in particular under the trademark "PARSOL 1789" by HOFFMANN LA ROCHE,
Isopropyl Dibenzoylmethane, Cinnamic Derivatives:
Ethylhexyl Methoxycinnamate sold in particular under the trademark "PARSOL MCX" by HOFFMANN LA ROCHE,
Isopropyl Methoxy cinnamate,
Isoamyl Methoxy cinnamate sold under the trademark "NEO HELIOPAN E 1000" by HAARMANN and REIMER,
Cinoxate,
DEA Methoxycinnamate,
Diisopropyl Methylcinnamate,
Glyceryl Ethylhexanoate Dimethoxycinnamate, β,β'-Diphenyl Acrylate Derivatives:
Octocrylene sold in particular under the trademark "UVINUL N539" by BASF,
Etocrylene, sold in particular under the trademark "UVINUL N35" by BASF, Benzophenone Derivatives:
Benzophenone-1 sold under the trademark "UVINUL 400" by BASF, Benzophenone-2 sold under the trademark "UVINUL D50" by BASF,
Benzophenone-3 or Oxybenzone, sold under the trademark "UVINUL M40" by BASF,
Benzophenone-4 sold under the trademark "UVINUL MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "UVINUL DS-49" by BASF,
Benzophenone-12,
n-Hexyl 2-(4-diethylamino-2-hydroxybenzoyl)benzoate,
Benzylidenecamphor Derivatives:
3-Benzylidene camphor manufactured under the name "MEXORYL SD" by CHIMEX,
4-Methylbenzylidene camphor sold under the name "EUSOLEX 6300" by MERCK,
Benzylidene Camphor Sulfonic Acid manufactured under the name "MEXORYL SL" by CHIMEX,
Camphor Benzalkonium Methosulfate manufactured under the name "MEXORYL SO" by CHIMEX,
Terephthalylidene Dicamphor Sulfonic Acid manufactured under the name "MESORYL SX" by CHIMEX,
Polyacrylamidomethyl Benzylidene Camphor manufactured under the name "MESORYL SW" by CHIMEX,
Benzimidazole Derivatives:
Phenylbenzimidazole Sulfonic Acid sold in particular under the trademark "EUSOLEX 232" by MERCK,
Disodium Phenyl Dibenzimidazole Tetra-sulfonate sold under the trademark "NEO HELIOPAN AP" by Haarmann and REIMER,
Triazine Derivatives:
Anisotriazine sold under the trademark "TINOSORB S" by CIBA SPECIALTY CHEMICALS,
Ethylhexyl triazone sold in particular under the trademark "UVINUL T150" by BASF,
Diethylhexyl Butamido Triazone sold under the trademark "UV-ASORB HEB" by SIGMA 3V,
2,4,6-Tris(diisobutyl 4'-aminobenzalmalonate)-s-triazine,
Benzotriazole Derivatives:
Drometrizole Trisiloxane sold under the name "Silatrizole" by RHODIA CHIMIE, Methylene bis-Benzotriazolyl Tetramethylbutylphenol, sold in solid form under the trademark "MIXXIM BB/100" by FAIRMOUNT CHEMICAL or in micronized form in aqueous dispersion under the trademark "TINOSORB M" by CIBA SPECIALTY CHEMICALS,
Anthranilic Derivatives:
Menthyl anthranilate sold under the trademark "NEO HELIOPAN MA" by Haarmann and REIMER,
Imidazoline Derivatives:
Ethylhexyl Dimethoxybenzylidene Dioxoimidazoline Propionate,
Benzalmalonate Derivatives:
Polyorganosiloxane with benzalmalonate functional groups such as polysilicone-15 sold under the trademark "PARSOL SLX" by HOFFMANN LAROCHE
Benzoxazole Derivatives:
2,4-Bis[5-1-(dimethylpropyl)benzoxazol-2-yl-(4-phenyl)imino]-6-(2-ethylhexyl)imino-1,3,5-triazine sold under the name Uvasorb K2A by Sigma 3V; and mixtures thereof.

The organic screening agents which are more particularly preferred are selected from among the following compounds:
Ethylhexyl Salicylate,
Ethylhexyl Methoxycinnamate,
Octocrylene,
Butyl Methoxydibenzoylmethane,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulfonic Acid,
Disodium Phenyl Dibenzimidazole Tetra-sulfonate,
2,4,6-Tris(diisobutyl 4'-aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl)imino]-6-(2-ethylhexyl)imino-1,3,5-triazine and mixtures thereof.

The additional inorganic screening agents are selected from among pigments or nanopigments (average size of the primary particles: generally between 5 nm and 100 nm, preferably between 10 nm and 50 nm) of metal oxides, coated or uncoated, such as for example nanopigments of titanium oxide (amorphous or crystallized in rutile and/or anatase form), iron oxide, zinc oxide, zirconium oxide or cerium oxide which are all UV photoprotective agents well known per se. Conventional coating agents are moreover alumina and/or aluminum stearate. Such nanopigments of metal oxides, coated or uncoated, are described in particular in EP-518,772 and E-518,773.

The additional screening agents according to the invention are generally present in the compositions according to the invention in an amount ranging from 0.1% to 30% by weight, and preferably from 0.5% to 15% by weight, relative to the total weight of the composition.

The compositions according to the invention may also contain agents for artificially bronzing and/or tanning the skin (self-tanning agents).

The self-tanning agents are generally selected from among mono- or polycarbonylated compounds such as for example isatin, alloxan, ninhydrin, glyceraldehyde, mesotartaric aldehyde, glutaraldehyde, erythrulose, derivatives of 4,5-pyrazolindiones as described in FR-2,466,492 and WO 97/35842, dihydroxyacetone (DHA), 4,4-dihydroxypyrazolin-5-one derivatives as described in EP-903,342. DHA will preferably be used.

DHA may be used in free form and/or encapsulated for example into lipid vesicles such as liposomes, which are described in particular in WO 97/25970.

The mono- or polycarbonylated self-tanning agents are generally present in the compositions according to the invention in proportions ranging from 0.1% to 10% by weight relative to the total weight of the composition, and preferably from 0.2% to 8% by weight relative to the total weight of the composition.

The compositions in accordance with the present invention may additionally comprise conventional cosmetic adjuvants, selected in particular from among organic solvents, ionic or nonionic thickeners, demulcents, humectants, opacifying agents, stabilizers, emollients, silicones, insect repellents, perfumes, preservatives, surfactants, fillers, active agents, pigments, polymers, propellants, alkanizing or acidifying agents or any other ingredient customarily used in the cosmetic and/or dermatological field.

Of course, one skilled in this art will be careful to choose the possible additional compound(s) cited above and/or their quantities such that the advantageous properties intrinsically attached to the compositions in accordance with the invention are not, or not substantially, impaired by the addition(s) envisaged.

Among the organic solvents lower alcohols and polyols may be mentioned.

Among the thickeners, there may be mentioned crosslinked acrylic polymers such as the Carbomers provided by Noveon, acrylate/C10–30 alkyl acrylate crosslinked polymers of the Pemulen type provided by Noveon or polyacrylate-3 sold under the name Viscophobe DB 1000 by Amerchol); polymers derived from acrylamido-2-methylpropanesulfonic acid (Hostacerin AMPS provided by Clariant, Sepigel 305 provided by SEPPIC), synthetic neutral polymers such as poly-N-vinylpyrrolidone, polysaccharides such as guar and xanthan gums, and modified or unmodified cellulose derivatives such as hydroxypropylated guar gum, methylhydroxyethylcellulose and hydroxypropylmethylcellulose.

The compositions according to the invention find application in a large number of treatments, in particular cosmetic treatments, of the skin, the lips and the hair, including the scalp, in particular for the protection and/or care of the skin, the lips and/or the hair, and/or for making up the skin and/or the lips.

The present invention also features the use of the compositions according to the invention as defined above for the manufacture of products for the cosmetic treatment of the skin, the lips and the hair, including the scalp, in particular for the protection and/or care of the skin, the lips and/or the hair, and/or for making up the skin and/or the lips.

The cosmetic compositions according to the invention may for example be used as care and/or sun protection product for the face and/or the body, having a liquid or semi-liquid consistency, such as milks, more or less unctuous creams, gel creams, pastes. They may be optionally packaged as an aerosol and provided in the form of a mousse or a spray.

The compositions according to the invention in the form of vaporizable fluid lotions in accordance with the invention are applied to the skin or the hair in the form of fine particles by means of pressurized devices. The devices in accordance with the invention are well known to persons skilled in the art and comprise nonaerosol pumps or "atomizers", the aerosol containers comprising a propellant and aerosol pumps using compressed air as propellant. The latter are described in U.S. Pat. Nos. 4,077,441 and 4,850,517.

The compositions packaged as an aerosol in accordance with the invention contain in general conventional propellants such as, for example, the hydrofluorinated compounds dichlorodifluoromethane, difluoroethane, dimethyl ether, isobutane, n-butane, propane, trichlorofluoromethane. They are preferably present in quantities ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example A

Moisturizing and Photoprotective Creams (O/W Emulsions Stabilized with Surfactants and Comprising a Crosslinked Gelling Copolymer Derived from AMPS)

| Ingredients | Emulsion 1 (not in accordance with the invention) | Emulsion 2 (invention) |
|---|---|---|
| Mixture of glyceryl monostearate and polyethylene glycol stearate (100 EO) 50/50 | 2.5 | 2.5 |
| Polyethylene glycol monostearate (50 EO) | 2.5 | 2.5 |
| Stearyl alcohol | 0.5 | 0.5 |
| Octyl methoxycinnamate | 7 | 7 |
| 1,1-dicarboxy-(2'2'-dimethylpropyl)-4,4-diphenylbutadiene (compound f) | 0 | 5 |
| $C_{12-15}$ alkyl benzoate | 10 | 10 |
| Glycerin | 3 | 3 |
| 3,3'-terephthalylidene-10,10'-dicamphorsulfonic acid | 5 | 0 |
| Ammonium polyacryldimethyltauramide (HOSTACERIN AMPS) | 1 | 1 |
| Triethanolamine | 3.55 | 0.01 |
| Preservative | 0.3 | 0.3 |
| Water | qs 100 | qs 100 |
| Viscosity (Pa · s) under 200 $s^{-1}$ (Rheomat 180) | 0.16 | 4.7 |

Mode of Preparation:

The surfactants and optionally the diarylbutadiene derivative are solubilized at 75° C. in the oily phase with stirring; the solution obtained is macroscopically homogeneous. Each emulsion is prepared by slowly introducing the oily phase into the aqueous phase with stirring with the aid of a Moritz-type homogenizer at 70° C. at a stirring speed of 2,000 rpm for 15 minutes. Each emulsion is then cooled to room temperature with gentle stirring.

After 24 hours at room temperature, it is observed that the emulsion 1 becomes liquid while the emulsion 2 according to the invention is in the form of a stable, brilliant cream which is pleasant to apply to the skin.

Example B

Photoprotective Milks (Surfactant-free O/W Emulsions Stabilized with a Non-Crosslinked Amphiphilic Copolymer Derived from AMPS)

| Ingredients | Emulsion 3 (not in accordance with the invention) | Emulsion 4 (invention) |
|---|---|---|
| Octyl methoxycinnamate | 7 | 7 |
| 1,1-dicarboxy-(2'2'-dimethylpropyl)-4,4-diphenylbutadiene (compound f) | 0 | 5 |
| $C_{12-15}$ alkyl benzoate | 10 | 10 |
| Glycerin | 3 | 3 |
| 3,3'-terephthalylidene-10,10'-dicamphorsulfonic acid | 5 | 0 |

-continued

| Ingredients | Emulsion 3 (not in accordance with the invention) | Emulsion 4 (invention) |
|---|---|---|
| Non-crosslinked copolymer of AMPS and an ester of (meth)acrylic acid and a polyoxyethylenated $C_{16}$–$C_{18}$ fatty alcohol containing 8 EO (GENAPOL T-080) such as that described in example 7 of application EP1059142 | 0.5 | 0.5 |
| Triethanolamine | 3.55 | 0.01 |
| Preservative | 0.3 | 0.3 |
| Water | qs 100 | qs 100 |
| Viscosity (Pa · s) under 200 $s^{-1}$ (Rheomat 180) | 0.04 | 0.15 |

Mode of Preparation:

The amphiphilic AMPS copolymer is solubilized for 2 hours, with stirring, in the aqueous phase at 25° C.; the solution obtained is macroscopically homogeneous. The emulsion is prepared by slowly introducing the oily phase into the aqueous phase with stirring with the aid of a Moritz-type homogenizer at a stirring speed of 2,000 rpm for 15 minutes.

The emulsion 3 becomes fluid and loses its viscosity. The emulsion 4 according to the invention remains stable and has a nice milk-type texture.

Example C

Photoprotective Creams (Surfactant-free O/W Emulsions Stabilized with an Amphiphilic Copolymer Derived from Crosslinked AMPS)

| Ingredients | Emulsion 5 (not in accordance with the invention) | Emulsion 6 (invention) |
|---|---|---|
| Octyl methoxycinnamate | 7 | 7 |
| 1,1-dicarboxy-(2'2'-dimethylpropyl)-4,4-diphenylbutadiene (compound f) | 0 | 5 |
| $C_{12-15}$ alkyl benzoate | 10 | 10 |
| Glycerin | 3 | 3 |
| 3,3'-terephthalylidene-10,10'-dicamphorsulfonic acid | 5 | 0 |
| Crosslinked copolymer of AMPS and an ester of (meth)acrylic acid and a polyoxyethylenated $C_{16}$–$C_{18}$ fatty alcohol containing 25 EO (GENAPOL T-250) such as that described in example 3 of application EP1059142 | 0.5 | 0.5 |
| Triethanolamine | 3.55 | 0.01 |
| Preservative | 0.3 | 0.3 |
| Water | qs 100 | qs 100 |
| Viscosity (Pa · s) under 200 $s^{-1}$ (Rheomat 180) | 0.05 | 0.70 |

Mode of Preparation:

The amphiphilic AMPS copolymer is solubilized for 2 hours, with stirring, in the aqueous phase at 25° C.; the solution obtained is macroscopically homogeneous. Each emulsion is prepared by slowly introducing the oily phase into the aqueous phase with stirring with the aid of a Moritz-type homogenizer at a stirring speed of 2,000 rpm for 15 minutes.

The emulsion 5 becomes macroscopically destabilized after 24 hours at room temperature, with the appearance of a phenomenon of creaming. The emulsion 6 remains stable and has a nice milk-type texture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective composition comprising at least one aqueous phase, at least one oily phase, at least one partially or completely neutralized, crosslinked or non-crosslinked water-soluble or water-dispersible acrylamido-2-methylpropanesulfonic acid (AMPS) polymer and at least one UV radiation-screening system, said at least one screening system comprising at least one 4,4-diarylbutadiene UV-A-screening agent.

2. The photoprotective composition as defined by claim 1, said at least one AMPS polymer being partially or completely neutralized with an inorganic or organic base.

3. The photoprotective composition as defined by claim 2, such neutralization being with sodium hydroxide, potassium hydroxide or aqueous ammonia.

4. The photoprotective composition as defined by claim 2, such neutralization being with mono-, di- or triethanolamine, aminomethylpropanediol, N-methylglucamine, basic amino acids and mixtures thereof.

5. The photoprotective composition as defined by claim 1, said at least one AMPS polymer being at least 90% neutralized.

6. The photoprotective composition as defined by claim 1, said at least one AMPS polymer being crosslinked with a crosslinking agent selected from among olefinically polyunsaturated compounds.

7. The photoprotective composition as defined by claim 6, said crosslinking agent being selected from among divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of the sugar series, or other allyl or vinyl ethers of polyfunctional alcohols, and the allyl esters of phosphoric and/or vinylphosphonic acid derivatives, or mixtures thereof.

8. The photoprotective composition as defined by claim 6, said crosslinking agent comprising methylenebisacrylamide, allyl methacrylate or trimethylolpropane triacrylate (TMPTA).

9. The photoprotective composition as defined by claim 1, the degree of crosslinking ranging from 0.01 to 10 mol % relative to the polymer.

10. The photoprotective composition as defined by claim 1, said at least one AMPS polymer being water-soluble or water-dispersible and selected from the group consisting of:

(i) crosslinked or non-crosslinked AMPS homopolymers;

(ii) crosslinked or non-crosslinked copolymers obtained from AMPS and from one or more hydrophilic ethylenically unsaturated monomers or hydrophobic ethylenically unsaturated monomers containing no fatty chain.

11. The photoprotective composition as defined by claim 10, said water-dispersible AMPS polymers having a molar mass ranging from 50,000 g/mol to 10,000,000 g/mol.

12. The photoprotective composition as defined by claim 10, the AMPS homopolymer comprising ammonium polyacryloyldimethyltauramide.

13. The photoprotective composition as defined by claim 10, the crosslinked or non-crosslinked copolymers of AMPS and of one or more hydrophilic or hydrophobic ethylenically unsaturated monomers being selected from among:

(a) copolymers of AMPS and acrylamide or methylacrylamide;

(b) copolymers of AMPS and vinylpyrrolidone or vinylformamide.

14. The photoprotective composition as defined by claim 13, the water-dispersible copolymer of AMPS being selected from among:

polyacrylamide/$C_{13}$–$C_{14}$ isoparaffin/laureth-7;

acrylamide/sodium acryloyldimethyltaurate/isohexadecane/polysorbate-80;

ammonium acryloyldimethyltaurate/VP copolymer.

15. The photoprotective composition as defined by claim 1, said at least one AMPS polymer being amphiphilic.

16. The photoprotective composition as defined by claim 15, said amphiphilic AMPS polymer comprising at least one fatty chain containing from 7 to 30 carbon atoms.

17. The photoprotective composition as defined by claim 15, said amphiphilic AMPS polymer having a weight-average molecular weight ranging from 50,000 to 10,000,000.

18. The photoprotective composition as defined by claim 15, said amphiphilic AMPS polymer comprising a random amphiphilic AMPS polymer modified by reaction with a $C_6$–$C_{22}$ n-monoalkylamine or di-n-alkylamine and optionally containing one or more ethylenically unsaturated hydrophilic monomers.

19. The photoprotective composition as defined by claim 15, said amphiphilic AMPS polymer being selected from among AMPS polymers from at least one ethylenically unsaturated monomer containing at least one hydrophobic part having from 7 to 30 carbon atoms and optionally one or more ethylenically unsaturated hydrophilic comonomers.

20. The photoprotective composition as defined by claim 19, said ethylenically unsaturated monomers containing at least one hydrophobic part having from 7 to 30 carbon atoms being selected from among acrylates and acrylamides of the following formula (1):

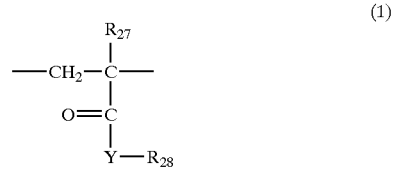

(1)

in which $R_{27}$ is a hydrogen atom, a linear or branched $C_1$–$C_6$ alkyl radical; Y is O or NH; and $R_{28}$ is a hydrophobic radical containing a fatty chain having from 7 to 22 carbon atoms.

21. The photoprotective composition as defined by claim 20, wherein formula (1), the hydrophobic radical $R_{28}$ is a saturated or unsaturated, linear or branched $C_7$–$C_{18}$ alkyl radical, $C_7$–$C_{18}$ perfluorinated alkyl radical, the cholesteryl radical or a cholesterol ester, or an aromatic polycyclic radical.

22. The photoprotective composition as defined by claim 20, wherein formula (1), the hydrophobic radical $R_{18}$ further contains at least one alkylene oxide structural unit.

23. The photoprotective composition as defined by claim 22, the number of moles of oxyalkylenated structural units ranging from 1 to 30 mol.

24. The photoprotective composition as defined by claim 20, the amphiphilic AMPS polymers comprising amphiphilic copolymers of:

(a) 2-acrylamido-2-methylpropanesulfonic acid (AMPS) structural units of the following formula (2):

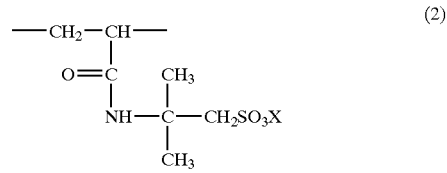

(2)

in which $X^+$ is a proton, an alkali metal cation, an alkaline earth metal cation or the ammonium ion; and (b) structural units of the following formula (3):

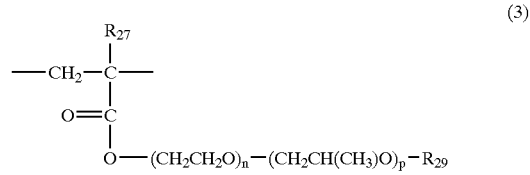

(3)

in which n and p, independently of each other, are each a number of moles and varies from 0 to 30, provided that n+p is less than or equal to 30; $R_{27}$ has the same meaning indicated above in formula (1) and $R_{29}$ is a linear or branched alkyl containing m carbon atoms ranging from 7 to 22.

25. The photoprotective composition as defined by claim 24, wherein formula (2), $X^+$ is sodium or ammonium.

26. The photoprotective composition as defined by claim 24, said amphiphilic AMPS polymers comprising:

(i) those which are non-crosslinked, in which p=0, n=7 or 25, $R_{27}$ is methyl and $R_{29}$ is a mixture of $C_{12}$–$C_{14}$ or $C_{16}$–$C_{18}$ alkyl, or (ii) those which are crosslinked, in which p=0, n=8 or 25, $R_{27}$ is methyl and $R_{29}$ is a mixture of $C_{16}$–$C_{18}$ alkyl.

27. The photoprotective composition as defined by claim 24, wherein the molar proportion of structural units of formula (3) ranges from 0.1 to 50%.

28. The photoprotective composition as defined by claim 24, wherein the molar proportion of structural units of formula (3) ranges from 50.1% to 99.9%.

29. The photoprotective composition as defined by claim 1, said at least one AMPS polymer comprising from 0.01% to 20% by weight relative to the total weight of the composition.

30. The photoprotective composition as defined by claim 1, said at least one 4,4-diarylbutadiene UV-A-screening agent having the following formula (I):

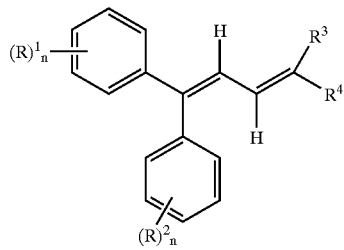

(I)

in which the diene system is of the Z,Z; Z,E; E,Z or E,E configuration or mixture of said configurations, and wherein:

$R^1$ and $R^2$, which may be identical or different, are each hydrogen, a $C_1$–$C_{20}$ alkyl radical, a $C_2$–$C_{10}$ alkenyl radical, a $C_1$–$C_{12}$ alkoxy radical, a $C_3$–$C_{10}$ cycloalkyl radical, a $C_3$–$C_{10}$ cycloalkenyl radical, a $C_1$–$C_{20}$ alkoxycarbonyl radical, a $C_1$–$C_{12}$ monoalkylamino radical, a $C_1$–$C_{12}$ dialkylamino radical, an aryl radical, a heteroaryl radical or a water-solubilizing substituent selected from among a carboxylate residue, a sulfonate residue or an ammonium residue;

$R^3$ is a group $COOR^5$, $COR^5$, $CONR^5R^6$, CN, O=S(—$R^5$)=O, O=S(—$OR^5$)=O, $R^7O$—P—(—$OR^8$)=O, a $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ cycloalkenyl radical, a $C_7$–$C_{10}$ bicycloalkenyl radical, an optionally substituted $C_6$–$C_{18}$ aryl radical an optionally substituted $C_3$–$C_7$ heteroaryl radical;

$R^4$ is a group $COOR^6$, $COR^6$, $CONR^5R^6$, CN, O=S(—$R^6$)=O, O=S(—$OR^6$)=O, $R^7O$—P—(—$OR^8$)=O, a $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ cycloalkenyl radical, a $C_7$–$C_{10}$ bicycloalkenyl radical, an optionally substituted $C_6$–$C_{18}$ aryl radical, an optionally substituted $C_3$–$C_7$ heteroaryl radical;

the radicals $R^5$ to $R^8$, which may be identical or different, are each hydrogen, a $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ bicycloalkenyl radical, a $C_7$–$C_{10}$ cycloalkenyl radical, an optionally substituted aryl radical, an optionally substituted heteroaryl radical; and n ranges from 1 to 3; with the proviso that the radicals $R^3$ to $R^8$ can together form, with the carbon atoms from which they depend, a $C_5$–$C_6$ ring which may be fused.

31. The photoprotective composition as defined by claim 30, wherein formula (I):

n=1 or 2;

$R^1$ and $R^2$, which may be identical or different, are each hydrogen, a $C_1$–$C_{20}$ alkyl radical, a $C_1$–$C_{12}$ alkoxy radical, a $C_1$–$C_{12}$ monoalkylamino radical, a $C_1$–$C_{12}$ dialkylamino radical, a water-solubilizing substituent selected from among a carboxylate group, a sulfonate group or an ammonium residue;

$R^3$ is a group $COOR^5$, $COR^5$, $CONR^5R^6$, a $C_1$–$C_{20}$ alkyl radical, a $C_3$–$C_{10}$ cycloalkyl radical, a $C_3$–$C_{10}$ cycloalkenyl radical, a $C_7$–$C_{10}$ bicycloalkyl radical, optionally substituted phenyl, naphthyl or thienyl;

$R^4$ is a group $COOR^6$, $COR^6$, $CONR^5R^6$, a $C_1$–$C_{20}$ alkyl radical, a $C_3$–$C_6$ cycloalkyl radical, a $C_3$–$C_{10}$ cycloalkenyl radical, a $C_7$–$C_{10}$ bicycloalkyl radical, optionally substituted phenyl, naphthyl or thienyl; and the radicals $R^5$ and $R^6$, which may be identical or different, are each hydrogen, a $C_1$–$C_{12}$ alkyl radical, a $C_3$–$C_{10}$ cycloalkyl radical, a $C_3$–$C_{10}$ cycloalkenyl radical, a $C_7$–$C_{10}$ bicycloalkyl radical, a $C_3$–$C_{10}$ bicycloalkenyl radical, optionally substituted phenyl or naphthyl.

32. The photoprotective composition as defined by claim 31, wherein formula (I):

$R^1$ and $R^2$, which may be identical or different, are each hydrogen, a $C_1$–$C_{20}$ alkyl radical, a $C_1$–$C_{20}$ alkoxy radical, a water-solubilizing substituent selected from among a carboxylate group, a sulfonate group or an ammonium residue;

$R^3$ is a group $COOR^5$, $COR^5$, $CONR^5R^6$;

$R^4$ is a group $COOR^6$, $COR^6$, $CONR^5R^6$; and the radicals $R^5$ and $R^6$, which may be identical or different, are each hydrogen, a $C_1$–$C_{12}$ alkyl radical, a $C_3$–$C_6$ cycloalkyl radical, a $C_3$–$C_{10}$ cycloalkenyl radical, a $C_7$–$C_{10}$ bicycloalkyl radical, a $C_3$–$C_{10}$ bicycloalkenyl radical, optionally substituted phenyl or naphthyl.

33. The photoprotective composition as defined by claim 32, the compound of formula (I) having the following formula (I'):

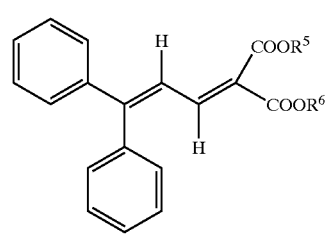

(I')

wherein the radicals $R^5$ and $R^6$, which may be identical or different, are each hydrogen, a $C_1$–$C_{20}$ alkyl radical, a $C_3$–$C_6$ cycloalkyl radical, a $C_3$–$C_{10}$ cycloalkenyl radical.

34. The photoprotective composition as defined by claim 33, the compound of formula (I') being 1,1-dicarboxy (2'2'dimethylpropyl)-4,4-diphenylbutadiene having the structure:

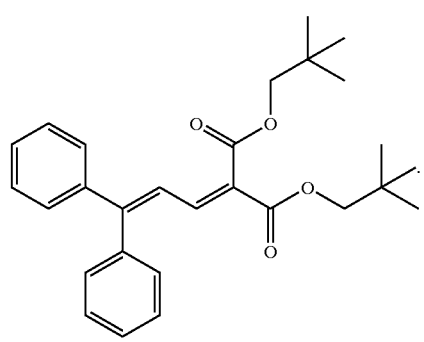

(compound f)

35. The photoprotective composition as defined by claim 1, said at least one 4,4-diarylbutadiene UV-A-screening agent having the following formula (II):

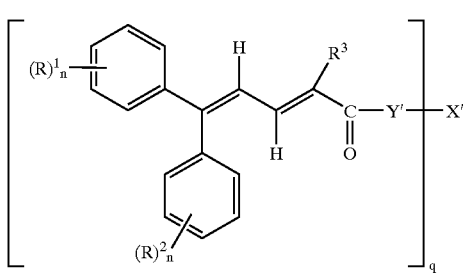

(II)

in which the diene system is of the Z,Z; Z,E; E,Z or E,E configuration or mixture of said configurations and wherein:

$R^1$, $R^2$, $R^3$ and n have the meanings indicated in the formula (I);

Y' is a group —O— or —$NR^9$—;

$R^9$ is hydrogen, a linear or branched $C_1$–$C_{20}$ alkyl radical, a $C_2$–$C_{10}$ alkenyl radical, a $C_3$–$C_{10}$ cycloalkyl radical, a $C_7$–$C_{10}$ bicycloalkyl radical, a $C_3$–$C_{10}$ cycloalkenyl radical, a $C_7$–$C_{10}$ bicycloalkenyl radical, an aryl radical, a heteroaryl radical;

X' is a residue of a linear or branched, aliphatic or cycloaliphatic $C_2$–$C_{20}$ polyol comprising from 2 to 10 hydroxyl groups and having the valency q; with the proviso that the carbon chain of said residue may be interrupted by one or more sulfur or oxygen atoms, one or more imine groups, one or more $C_1$–$C_4$ alkylimino groups; and q ranges from 2 to 10.

36. The photoprotective composition as defined by claim 35, wherein formula (II):

$R^1$ and $R^2$, which may be identical or different, are each hydrogen, a $C_1$–$C_{12}$ alkyl radical, a $C_1$–$C_8$ alkoxy radical, a water-solubilizing substituent selected from among a carboxylate group, a sulfonate group or an ammonium residue;

$R^3$ is a group $COOR^5$, $CONR^5R^6$, CN, a $C_3$–$C_{10}$ cycloalkyl radical, a $C_7$–$C_{10}$ bicycloalkyl radical;

$R^5$ and $R^6$, which may be identical or different, are each a linear or branched $C_1$–$C_{20}$ alkyl radical, a $C_3$–$C_{10}$ cycloalkyl radical, a $C_7$–$C_{10}$ bicycloalkyl radical, optionally substituted naphthyl or phenyl; and X' is a $C_2$–$C_{20}$ polyol residue comprising from 2 to 6 hydroxyl groups.

37. The photoprotective composition as defined by claim 36, wherein formula (II), X' is an ethanol or pentaerythritol residue.

38. The photoprotective composition as defined by claim 37, said compound of formula (II) being selected from among the following compounds:

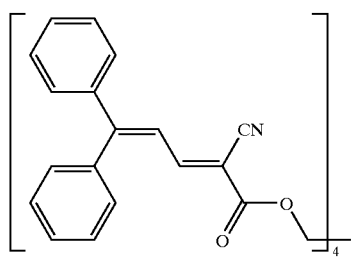

(compound g)

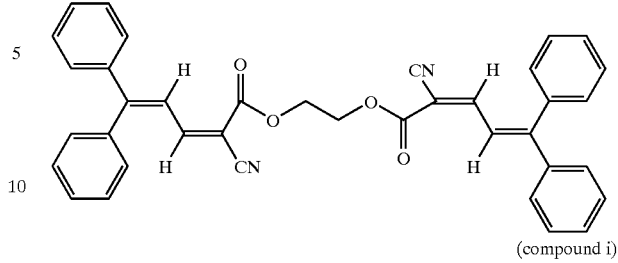

(compound h)

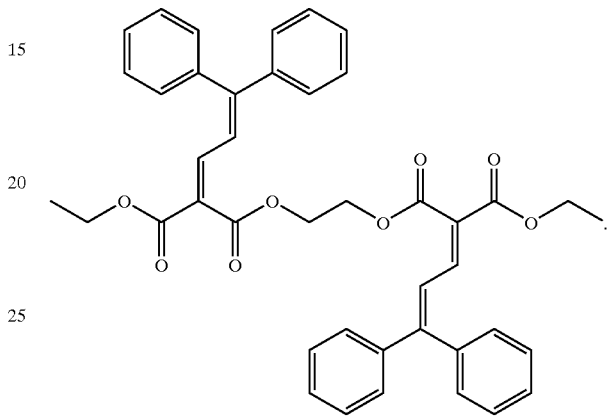

(compound i)

39. The photoprotective composition as defined by claim 1, said at least one 4,4-diarylbutadiene compound constituting from 0.1% to 20% by weight relative to the total weight of the emulsion.

40. The photoprotective composition as defined by claim 1, further comprising at least one additional organic or inorganic sunscreening agent active in the UV-A and/or UV-B regions, water-soluble, fat-soluble or insoluble in the usual cosmetic solvents.

41. The photoprotective composition as defined by claim 40, comprising at least one additional organic screening agent selected from among the anthranilates; cinnamic derivatives; dibenzoylmethane derivatives; salicylic derivatives, camphor derivatives; triazine derivatives; benzophenone derivatives; β,β'-diphenyl acrylate derivatives; benzotriazole derivatives; benzalmalonate derivatives; benzimidazole derivatives; imidazolines; bis-benzoazolyl derivatives; p-aminobenzoic acid (PABA) derivatives; benzoxazole derivatives; methylenebis (hydroxyphenylbenzotriazole) derivatives; screening polymers and screening silicones; dimers derived from α-alkylstyrene and mixtures thereof.

42. The photoprotective composition as defined by claim 41, said at least one additional organic screening agent comprising:

Ethylhexyl Salicylate,
Ethylhexyl Methoxycinnamate,
Octocrylene,
Butyl Methoxydibenzoylmethane,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulfonic acid, Disodium Phenyl Dibenzimidazole Tetra-sulfonate,
2,4,6-Tris(4'-diisobutyl aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl)imino]-6-(2-ethylhexyl)imino-1,3,5-triazine,
and mixtures thereof.

43. The photoprotective composition as defined by claim 40, comprising at least one additional inorganic screening agent selected from among pigments or nanopigments of metal oxides, whether coated or uncoated.

44. The photoprotective composition as defined by claim 43, said at least one additional inorganic screening agent comprising nanopigments of titanium oxide, which is amorphous or crystallized, in rutile and/or anatase form, iron oxide, zinc oxide, zirconium oxide or cerium oxide.

45. The photoprotective composition as defined by claim 1, further comprising at least one agent for artificial bronzing and/or tanning of the skin.

46. The photoprotective composition as defined by claim 1, further comprising at least one cosmetic adjuvant selected from among organic solvents, ionic or nonionic thickeners, demulcents, humectants, opacifying agents, stabilizers, emollients, silicones, insect repellents, perfumes, preservatives, surfactants, fillers, active agents, pigments, polymers, propellants, alkalinizing or acidifying agents or any other ingredient commonly employed in the cosmetic and/or dermatological field.

47. The photoprotective composition as defined by claim 1, formulated as a dispersion of the lotion or serum type, an oil-in-water or water-in-oil emulsion, a multiple emulsion, a microemulsion, a vesicular dispersion of the ionic and/or nonionic type or a wax/aqueous phase dispersion.

48. The photoprotective composition as defined by claim 1, formulated as an oil-in-water or water-in-oil emulsion containing at most 1% by weight of emulsifying surfactant relative to the total weight of the composition.

49. A method for the photoprotection of the skin, lips and/or hair against the damaging effects of UV-radiation, comprising topically applying thereon, a thus effective amount of a photoprotective composition comprising at least one aqueous phase, at least one oily phase, at least one partially or completely neutralized, crosslinked or non-crosslinked water-soluble or water-dispersible acrylamido-2-methylpropanesulfonic acid (AMPS) polymer and at least one UV radiation-screening system, said at least one screening system comprising at least one 4,4-diarylbutadiene UV-A-screening agent.

* * * * *